(12) United States Patent  
Hills (10) Patent No.: US 7,987,722 B2
(45) Date of Patent: Aug. 2, 2011

(54) ULTRASONIC AIR AND FLUID DETECTOR (75) Inventor: Chris Hills, Layton, UT (US)

(73) Assignee: ZEVEX, Inc., Salt Lake City, UT (US)

( * ) Notice: Subject to any disclaimer, the term of this patent is extended or adjusted under 35 U.S.C. 154(b) by 328 days.

(21) Appl. No.: 12/196,827

(22) Filed: Aug. 22, 2008

(65) Prior Publication Data

US 2009/0049919 A1   Feb. 26, 2009

Related U.S. Application Data (60) Provisional application No. 60/957,973, filed on Aug. 24, 2007.

(51) Int. Cl.
 G01N 29/14 (2006.01)
 A61B 8/14 (2006.01)
(52) U.S. Cl. ............ 73/632; 73/649; 600/437; 600/459
(58) Field of Classification Search ............... 73/632, 73/715, 721, 723, 727, 114.21, 152.22, 152.27; 600/437, 459
 See application file for complete search history.

(56) References Cited

U.S. PATENT DOCUMENTS

| 3,090,222 A | 5/1963 | Akaboshi et al. |
| 3,450,476 A | 6/1969 | Rando |
| 3,588,859 A | 6/1971 | Petree |
| 3,939,360 A | 2/1976 | Jackson |
| 3,974,681 A | 8/1976 | Namery |
| 3,987,674 A | 10/1976 | Baumoel |
| 3,994,599 A | 11/1976 | Southwell |
| 4,002,996 A | 1/1977 | Kebanoff et al. |
| 4,054,255 A | 10/1977 | Magenheim |
| 4,068,521 A | 1/1978 | Cosentino et al. |
| 4,083,038 A | 4/1978 | Kebanoff |
| 4,144,517 A | 3/1979 | Baumoel |
| 4,183,007 A | 1/1980 | Baird |
| 4,193,004 A | 3/1980 | Lobdell et al. |
| 4,277,711 A | 7/1981 | Hanafy |
| 4,280,126 A | 7/1981 | White |
| 4,312,341 A | 1/1982 | Zissimopoulos et al. |
| 4,399,362 A | 8/1983 | Cormier et al. |
| 4,492,463 A | 1/1985 | Marcuse et al. |
| 4,559,454 A | 12/1985 | Kramer |
| 4,580,448 A | 4/1986 | Skrgatic |
| 4,618,261 A | 10/1986 | Flanders et al. |
| 4,631,529 A | 12/1986 | Zeitz |

(Continued)

FOREIGN PATENT DOCUMENTS

DE  3241033  5/1984

(Continued)

OTHER PUBLICATIONS

International Search Report for PCT/US08/074064, Mailed Nov. 13, 2008.

(Continued)

*Primary Examiner* — Jacques M Saint Surin
(74) *Attorney, Agent, or Firm* — Bateman IP Law Group (57) ABSTRACT

An ultrasonic sensor for detecting the presence of air or liquid uses flex circuits for connecting the ceramic element to the driver circuitry. The sensor provides improved transmission of ultrasonic signals between the ceramic element and the adjacent material, providing greater flexibility in using the sensor.

18 Claims, 10 Drawing Sheets

U.S. PATENT DOCUMENTS

| | | | |
|---|---|---|---|
| 4,663,965 | A | 5/1987 | Metcalf et al. |
| 4,689,986 | A | 9/1987 | Carson et al. |
| 4,722,224 | A | 2/1988 | Scheller et al. |
| 4,749,988 | A | 6/1988 | Berman et al. |
| 4,762,518 | A | 8/1988 | Kreinick |
| 4,821,558 | A | 4/1989 | Pastrone et al. |
| 4,829,448 | A | 5/1989 | Balding et al. |
| 4,833,918 | A | 5/1989 | Jean et al. |
| 4,881,487 | A | 11/1989 | Moore |
| 4,884,065 | A | 11/1989 | Crouse et al. |
| 4,896,099 | A | 1/1990 | Suzuki |
| 4,908,676 | A | 3/1990 | Bedell et al. |
| 4,920,336 | A | 4/1990 | Meijer |
| 4,998,022 | A | 3/1991 | Tregay |
| 5,025,222 | A | 6/1991 | Scott et al. |
| 5,053,747 | A | 10/1991 | Slate et al. |
| 5,074,659 | A | 12/1991 | Suzuki et al. |
| 5,116,759 | A | 5/1992 | Klainer et al. |
| 5,121,628 | A | 6/1992 | Merkl et al. |
| 5,176,631 | A | 1/1993 | Koenig |
| 5,182,947 | A | 2/1993 | Fidelak et al. |
| 5,191,795 | A | 3/1993 | Fellingham et al. |
| 5,229,726 | A | 7/1993 | Kent |
| 5,233,319 | A | 8/1993 | Mizan et al. |
| 5,260,665 | A | 11/1993 | Goldberg et al. |
| 5,267,221 | A * | 11/1993 | Miller et al. .............. 367/140 |
| 5,295,120 | A | 3/1994 | McShane |
| 5,303,585 | A | 4/1994 | Lichte |
| 5,305,237 | A | 4/1994 | Dalrymple et al. |
| 5,351,521 | A | 10/1994 | Cracknell |
| 5,392,638 | A | 2/1995 | Kawahara |
| 5,394,732 | A | 3/1995 | Johnson et al. |
| 5,417,672 | A | 5/1995 | Nita et al. |
| 5,422,495 | A | 6/1995 | Cohn |
| 5,438,868 | A | 8/1995 | Holden et al. |
| 5,442,495 | A | 8/1995 | Saito et al. |
| 5,455,565 | A | 10/1995 | Moeenziai et al. |
| 5,456,887 | A | 10/1995 | Calvo et al. |
| 5,460,178 | A | 10/1995 | Hudon et al. |
| 5,475,350 | A | 12/1995 | Yamada et al. |
| 5,485,743 | A | 1/1996 | Taherian et al. |
| 5,499,077 | A | 3/1996 | Endo et al. |
| 5,514,102 | A | 5/1996 | Winterer et al. |
| 5,531,680 | A | 7/1996 | Dumas et al. |
| 5,534,708 | A | 7/1996 | Ellinger et al. |
| 5,541,468 | A * | 7/1996 | Frey et al. .............. 310/334 |
| 5,557,368 | A | 9/1996 | Endo et al. |
| 5,672,887 | A | 9/1997 | Shaw et al. |
| 5,680,111 | A | 10/1997 | Danby et al. |
| D389,228 | S | 1/1998 | Winterer et al. |
| 5,704,584 | A | 1/1998 | Winterer et al. |
| 5,720,721 | A | 2/1998 | Dumas et al. |
| 5,723,773 | A | 3/1998 | Bryan |
| 5,733,061 | A | 3/1998 | Child |
| 5,746,756 | A | 5/1998 | Bromfield et al. |
| 5,764,356 | A | 6/1998 | Iwase et al. |
| 5,789,675 | A | 8/1998 | Blaine et al. |
| 5,798,050 | A | 8/1998 | Gaynes et al. |
| 5,810,323 | A | 9/1998 | Winterer et al. |
| 5,844,587 | A | 12/1998 | Ando et al. |
| 5,920,007 | A | 7/1999 | Hirota et al. |
| 6,023,970 | A | 2/2000 | Blaine |
| 6,064,577 | A | 5/2000 | Moskowitz et al. |
| 6,068,612 | A | 5/2000 | Bowman et al. |
| 6,069,433 | A | 5/2000 | Lazarus et al. |
| 6,110,153 | A | 8/2000 | Davis et al. |
| 6,110,314 | A * | 8/2000 | Nix et al. .............. 156/218 |
| 6,142,008 | A | 11/2000 | Cole et al. |
| 6,142,979 | A | 11/2000 | McNally et al. |
| 6,192,752 | B1 | 2/2001 | Blaine |
| 6,238,347 | B1 * | 5/2001 | Nix et al. .............. 600/463 |
| 6,328,720 | B1 | 12/2001 | McNally et al. |
| D455,489 | S | 4/2002 | Beck et al. |
| 6,396,583 | B1 | 5/2002 | Clare |
| 6,408,679 | B1 | 6/2002 | Kline-Schoder et al. |
| 6,506,035 | B1 | 1/2003 | Beck |
| 6,523,414 | B1 | 2/2003 | Malmstrom et al. |
| 6,531,708 | B1 | 3/2003 | Malmstrom et al. |
| 6,543,885 | B2 | 4/2003 | Bahl et al. |
| 6,595,950 | B1 | 7/2003 | Miles et al. |
| 6,623,447 | B2 | 9/2003 | Miles et al. |
| 6,636,010 | B1 | 10/2003 | Malmstrom et al. |
| 6,659,976 | B2 | 12/2003 | Beck et al. |
| 6,685,670 | B2 | 2/2004 | Miles et al. |
| 6,709,392 | B1 | 3/2004 | Salgo et al. |
| 6,749,591 | B1 | 6/2004 | McNally et al. |
| 6,750,468 | B2 | 6/2004 | Malmstrom et al. |
| 6,776,763 | B2 * | 8/2004 | Nix et al. .............. 600/466 |
| D501,924 | S | 2/2005 | Cise et al. |
| 6,852,094 | B2 | 2/2005 | Beck et al. |
| D503,799 | S | 4/2005 | Beck |
| D503,978 | S | 4/2005 | Beck |
| D504,506 | S | 4/2005 | Beck et al. |
| D505,199 | S | 5/2005 | Beck et al. |
| 6,902,541 | B2 | 6/2005 | McNally et al. |
| 6,907,788 | B2 | 6/2005 | Malmstrom et al. |
| D507,647 | S | 7/2005 | Beck et al. |
| 6,923,785 | B2 | 8/2005 | Miles et al. |
| 6,932,114 | B2 | 8/2005 | Sparks |
| 6,949,376 | B2 | 9/2005 | Kluttz |
| 6,979,311 | B2 | 12/2005 | Miles et al. |
| D523,553 | S | 6/2006 | Beck et al. |
| 7,070,575 | B2 | 7/2006 | Beck et al. |
| 7,121,143 | B2 | 10/2006 | Malmstrom et al. |
| 7,150,727 | B2 | 12/2006 | Cise et al. |
| 7,152,482 | B2 | 12/2006 | Ueno et al. |
| D536,783 | S | 2/2007 | Cise et al. |
| 7,201,870 | B2 | 4/2007 | Olsen et al. |
| 7,367,963 | B2 | 5/2008 | Cise et al. |
| 2002/0169424 | A1 | 11/2002 | Miles et al. |
| 2002/0192111 | A1 | 12/2002 | Divino, Jr. et al. |
| 2003/0055375 | A1 | 3/2003 | Holst et al. |
| 2004/0197223 | A1 | 10/2004 | Olsen et al. |
| 2004/0220542 | A1 | 11/2004 | Cise et al. |
| 2005/0004540 | A1 | 1/2005 | McNally |
| 2005/0119625 | A1 | 6/2005 | Miles et al. |
| 2005/0234407 | A1 | 10/2005 | Spohn et al. |
| 2006/0058740 | A1 | 3/2006 | Cise |
| 2007/0118078 | A1 | 5/2007 | McNally |
| 2007/0151346 | A1 | 7/2007 | Malmstrom et al. |
| 2007/0167752 | A1 | 7/2007 | Proulx et al. |
| 2008/0098798 | A1 | 5/2008 | Riley |
| 2008/0103445 | A1 | 5/2008 | Blaine et al. |
| 2008/0119782 | A1 | 5/2008 | Steinman |
| 2008/0134750 | A1 | 6/2008 | Riley |
| 2008/0208117 | A1 | 8/2008 | Steinman |
| 2009/0049919 | A1 | 2/2009 | Hills |
| 2009/0149801 | A1 | 6/2009 | Crandall |
| 2009/0192367 | A1 | 7/2009 | Braig et al. |
| 2009/0254034 | A1 | 10/2009 | Beck |

FOREIGN PATENT DOCUMENTS

| | | |
|---|---|---|
| JP | 61-3012 | 1/1986 |
| JP | 2005-337937 | 12/2005 |
| WO | WO 89/01796 | 3/1989 |
| WO | WO 98/04301 | 2/1998 |

OTHER PUBLICATIONS

International Preliminary Report on Patentability from related PCT application, mailed Mar. 4, 2010.

* cited by examiner

ULTRASONIC AIR AND FLUID DETECTOR

RELATED APPLICATIONS

The present application claims the benefit of U.S. Provisional Application Ser. No. 60/957,973, filed Aug. 24, 2007, which is expressly incorporated herein in its entirety.

BACKGROUND OF THE INVENTION

1. The Field of the Invention

The present invention relates to an ultrasonic detector for use in detecting air and liquid in a chamber.

2. State of the Art

In many situations, it is desirable to detect the presence of air or liquid in a location. For example, it may be desirable to detect whether air or liquid is present in a reservoir or container to thereby determine whether the container is full or empty. It may also be desirable to detect the presence of air or liquid in a conduit such as a pipe or tube. It may be desirable to detect air in a liquid stream, or to detect liquid in a gas stream. The proper detection of gas or liquid at desired locations in a system may improve the safety or efficiency of the system by allowing the system operation to be changed to prevent any undesired effects of the liquid or gas.

The present invention provides an improved ultrasonic sensor and methods of operating the same.

SUMMARY OF THE INVENTION

It is an object of the present invention to provide an improved ultrasonic sensor and methods for operating the same.

According to one aspect of the invention, an ultrasonic sensor is provided which utilizes a flex circuit for electrical contact with a ceramic element. The flex circuit may be attached to the ceramic element with a conductive adhesive, such as an anisotropic conductive epoxy, which eliminates the need for soldering to the ceramic element or other types of attachment.

According to another aspect of the invention, the flex circuit provides an integral matching layer between the resulting piezoelectric sensor and the surrounding material. The matching layer improves the transmission of ultrasonic signals between the sensor and the surrounding material (such as the housing, tube, or reservoir) and allows for improved modes of operating the sensor.

These and other aspects of the present invention are realized in a ultrasonic sensor as shown and described in the following figures and related description.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

Figures 1, 2:
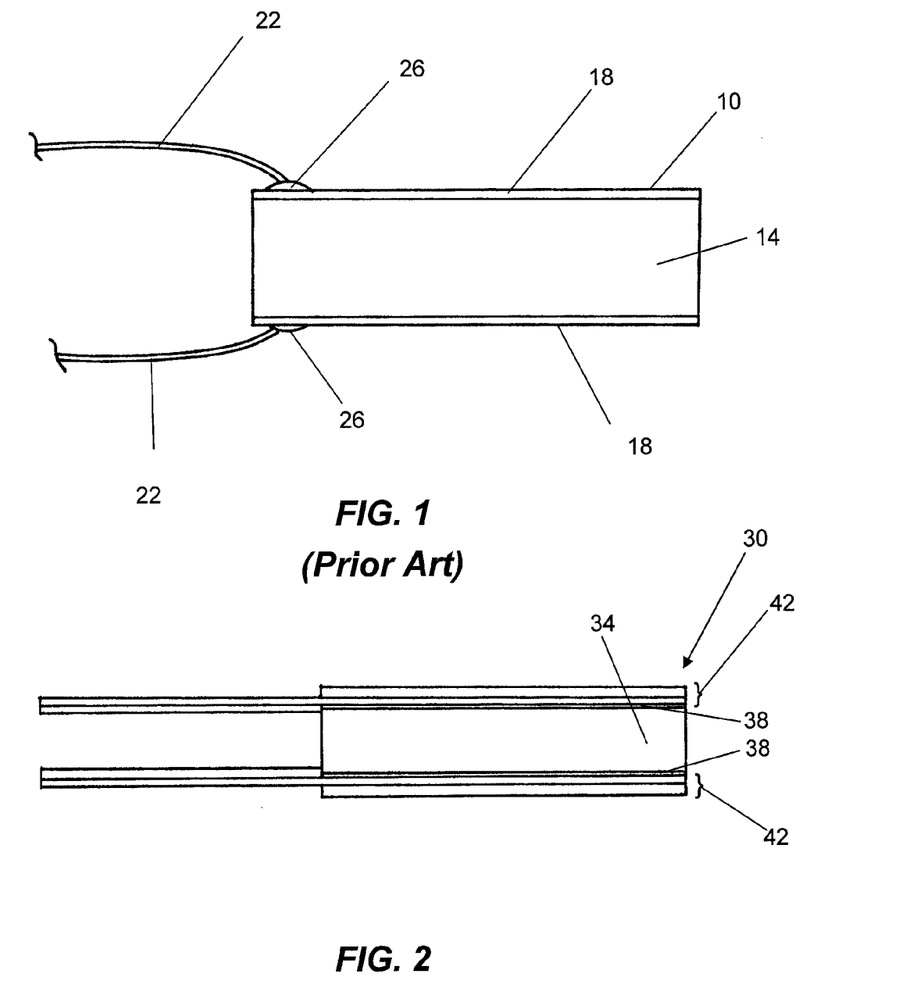
FIG. 1 shows a side view of a prior art piezoelectric sensor.
FIG. 2 shows a side view of a sensor of the present invention.

Turning now to FIG. 1, a side view of a typical prior art piezoelectric sensor element is shown. The piezoelectric sensor 10 includes a ceramic element 14 which has layers of silver 18 deposited on two opposing sides of the ceramic. Electrical leads 22 are attached to the silver layers 18 with solder 26. Conventional methods of electrical connection to the ceramic element may pose difficulty as they result in an uneven surface which may be more difficult to adequately couple to the housing or structures surrounding the sensor 10.

FIG. 2 shows a side view of a piezoelectric (ultrasonic) sensor 30 according to the present invention. The sensor 30 includes a ceramic element 34 with silver layers 38 deposited on two opposing sides of the ceramic. Other metal contact layers may be used on the ceramic, but silver is commonly used. The sensor 30 also includes two flex circuits 42 which form electrical attachments to the silver layers 38 of the ceramic element 34 and also form leads for connecting the completed sensor 30 to a driver circuit (not shown).

Figure 3:
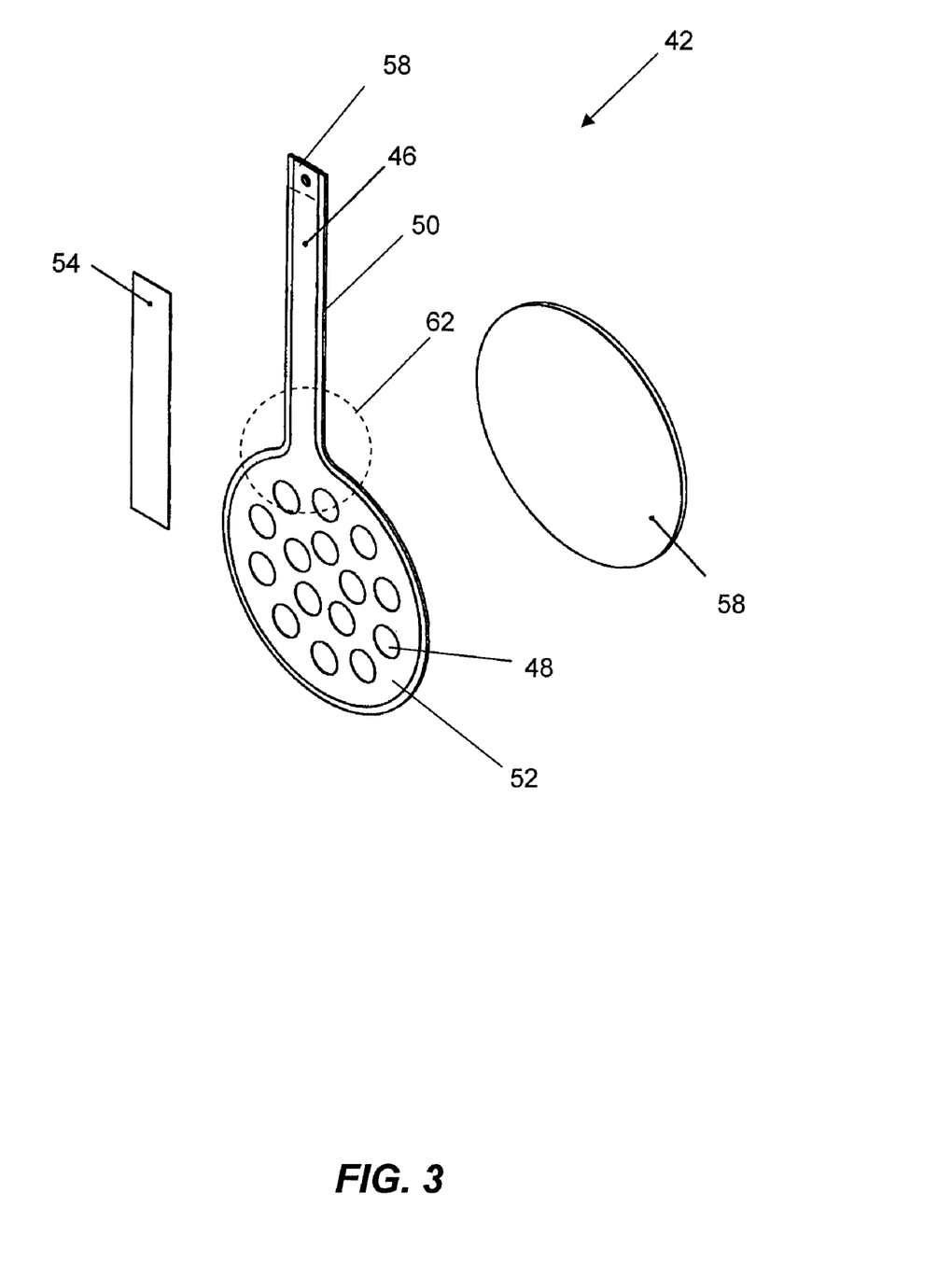
FIG. 3 shows an exploded perspective view of a flex circuit of the sensor of FIG. 2.

FIG. 3 shows an exploded perspective view of a flex circuit 42 as shown in FIG. 2. The flex circuit 42 includes a copper contact 46 (shown as a copper contact layer, although it will be appreciated that other materials such as silver or gold maybe used for the contact layer) which contacts the metal layer 38 (FIG. 2) on the ceramic element 34 (FIG. 2) and which forms an electrical lead for the completed sensor. The copper contact 46 is adhered to an insulating layer 50 (preferably a polyimide layer). The copper contact 46 may include a plurality of holes 48 formed therein in the area which is adhered to the ceramic element. The holes 48 provide a recess for adhesive (such as the anisotropic epoxy) and allow for better contact between the copper contact 46 and the metal layer 38 of the ceramic element 34. A currently preferred material for the insulating layer 50 is a polyimide, such as KAPTON®.

A rectangular piece of insulating material 54, such as the polyimide, may be used to cover a portion of the copper contact 46 which forms the electrical lead, leaving a small rectangular tab 58 of copper exposed for electrical connection. A disk 58 of the insulating material (such as the polyimide) may be adhered to the back of the insulating layer 50 to adjust the thickness of the polyimide and create a matching layer which aids in the transmission of the ultrasound signals between the ceramic element and the material used in the housing or conduit (which is often plastic). The flex circuit 42 is shown for a round piezoelectric sensor, and as such the copper contact 46 includes a round contact pad 52 for making electrical contact with the ceramic element 34. Other shapes may be made depending on the particular design requirements of the sensor.

Figure 4:
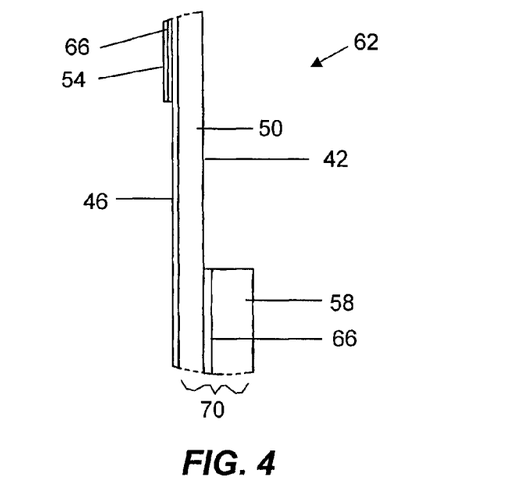
FIG. 4 shows a close-up view of the flex circuit of FIG. 3.

FIG. 4 shows a close up side view of the area designated at 62 of FIG. 3 for an assembled flex circuit 42. An adhesive 66 may be used to attach the various polyimide layers to the copper contact 46 and to each other. It is desirable that the adhesive and the attachment between the various layers of the flex circuit 42 do not contain air bubbles, as air bubbles will interfere with the transmission of ultrasonic signals.

According to one aspect of the invention, the flex circuit 42 provides a copper contact 46 which serves as both an electrical connection to the ceramic element and as an electrical lead for connection to the driver circuitry. Additionally, the copper contact 46, when attached to the ceramic element, does not result in a bump or uneven surface which is more difficult to acoustically couple the sensor to the housing or reservoir when using the completed sensor. The combined thickness 70 of the polyimide layers 50 and 58 is determined so as to create a matching layer between the ceramic element 34 and the reservoir or housing wall, which is usually plastic. The matching layer reduces the resistance to transmission of the ultrasound signals by reducing signal reflections at the juncture of materials with different acoustic properties.

The polyimide layers 50, 58 used in making the flex circuit 42 make the resulting sensor more sensitive and reduce the time for the ceramic element to stop oscillating after producing an ultrasonic signal and, as such, make the sensor more sensitive and allow for use in systems not previously suited for this type of sensor. A particular advantage of the polyimide layers integrated into the flex circuit is that they allow for the use of cheaper and more commonly available ceramics as the ceramic element. Previously, a lead metaniobate ceramic was used as the ceramic in sensors as described herein. The lead metaniobate ceramic is not widely available and is relatively expensive. The construction of the flex circuit allows for the use of lead zirconate titanate ceramic, which is cheaper and more available. The lead zirconate titanate ceramic has previously not been suitable for use in the sensors as described herein as it was not particularly efficient in transmitting and receiving signals.

The flex circuits 42 also aid in temperature and frequency sensitivity of the sensor 30. By improving the transmission of the ultrasonic signal, the flex circuit 42 allows for single pulse driving of the sensor 30. The combination of the flex circuit 42 and single pulse driving reduces the resonance changes of the sensor 30 with temperature and improves the acoustic coupling of the sensor across a wider range of frequencies, making the sensor 30 more versatile and less sensitive to changes in temperature or operating frequency. Additionally, the use of a single pulse drive and the reduced sensitivity to changes in operating frequency and temperature allow for significant simplification of the drive circuitry, making it easier to make the circuitry integral to the sensor. This prevents the transmission of analog signals across longer lengths of wire, and thus improves the performance of the sensor by reducing noise and signal loss.

According to a present embodiment, the ceramic element 34 is round and has a diameter of about 0.250 inch and a thickness of about 0.040 inch, and is coated on the two flat sides with a silver layer. The combined thickness 70 of the polyimide layers 50, 58 is optimally about 0.010 inch. The thickness 70 may vary slightly according to the availability of materials, and thus may be 0.009 inch or 0.011, etc. A smaller detector may be made by using a ceramic element 34 with a thickness of about 0.017 inch and a thickness 70 of the polyimide layers of about 0.004 inch. Such a smaller sensor would improve the response time of the sensor and allow for use on smaller conduits or reservoirs.

Another advantage of the present invention is that the flex circuit assemblies 42 allow for easier construction and assembly of the piezoelectric sensors 30. The flex circuit 42 may be easily manufactured using existing techniques, and may be attached to the ceramic element in a variety of methods. If desired, a small amount of solder may be placed on the metal layer 38 of the ceramic element 34, and the copper disk 52 of the flex circuit 42 may be hot pressed against the ceramic to melt the solder and adhere the flex circuit. Alternatively, an adhesive may be used to attach the flex circuit to the ceramic element. It has been found that a conductive adhesive may not be necessary if adequate pressure is applied to ensure that the copper contact 46 contacts the metal layer 38 on the ceramic element 34. Currently, an anisotropic epoxy is a preferred adhesive as it ensures conduction between the metal layer 38 on the ceramic element 34 and the copper contact 46, but will not short circuit the sensor if the anisotropic epoxy bridges the two flex circuits 42 on either side of the chip.

Figure 5:
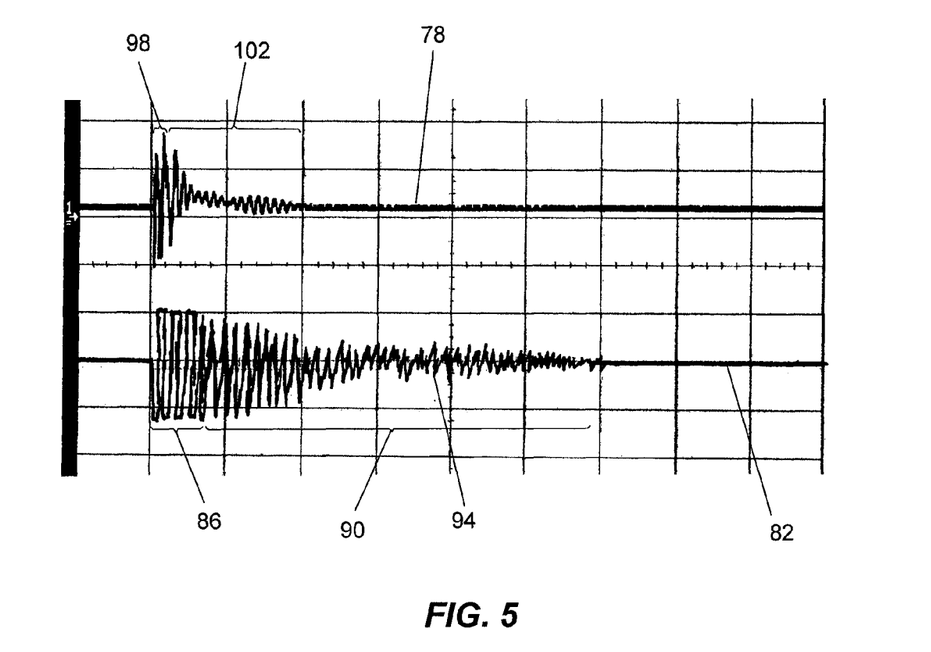
FIG. 5 shows activity of the ceramic element of the sensors of FIG. 1 and FIG. 2.

FIG. 5 illustrates typical electrical responses for transmitting an ultrasonic signal from a prior art ultrasonic sensor and for an ultrasonic sensor of the present invention. The electrical response 78 is typical for a piezoelectric sensor of the present invention and the electrical response 82 is typical for a prior art piezoelectric sensor. Because of the less efficient transmission and reception of the ultrasonic signals between the prior art sensor and the surrounding material (typically a conduit or housing), the prior art sensor is typically driven for about 5 periods of oscillation by the driver circuit as indicated at 86. Thus, a driving electrical signal is applied during time period 86 to increase the energy transmitted from the sensor and thereby increase the strength of the signal which is transmitted through the desired conduit or reservoir.

After the driven period 86, the prior art sensor undergoes a ring down period 90 where continued vibrations and resultant electrical charges 94 are present in the ceramic element. Thus, the signal transmitted from the prior art sensor is not a sharp and clearly delineated signal, but is one which gradually diminishes over a period of time. The extended ring down period 90 of the prior art sensor makes it more difficult to detect incoming signals during this time period. This limits the use of these sensors to situations where any received signals would come after the driven period 86 and the ring down period 90. Thus, prior art sensors have been used on larger reservoirs where an ultrasonic signal reflected off of the far side of a liquid filled reservoir will arrive after the ring down period 90.

The flex circuits 42 of the sensor 30 of the present invention provide for much more efficient transfer of ultrasonic vibrations into and out of the sensor. As shown by the electrical response 78 of the sensor 30, the more efficient transmission of signals into and out of the sensor 30 allow for a shorter driven period 98, such as a single oscillation of the ceramic element 34. Additionally, the ring down period 102 is reduced as vibrations are more quickly transmitted out of the ceramic element 34 and into the adjacent conduit or reservoir. The sensor 30 is thus able to detect incoming ultrasonic signals occurring quickly after the driven period, making the sensor useful for single sided detection of small reservoirs and conduits.

Figure 6:
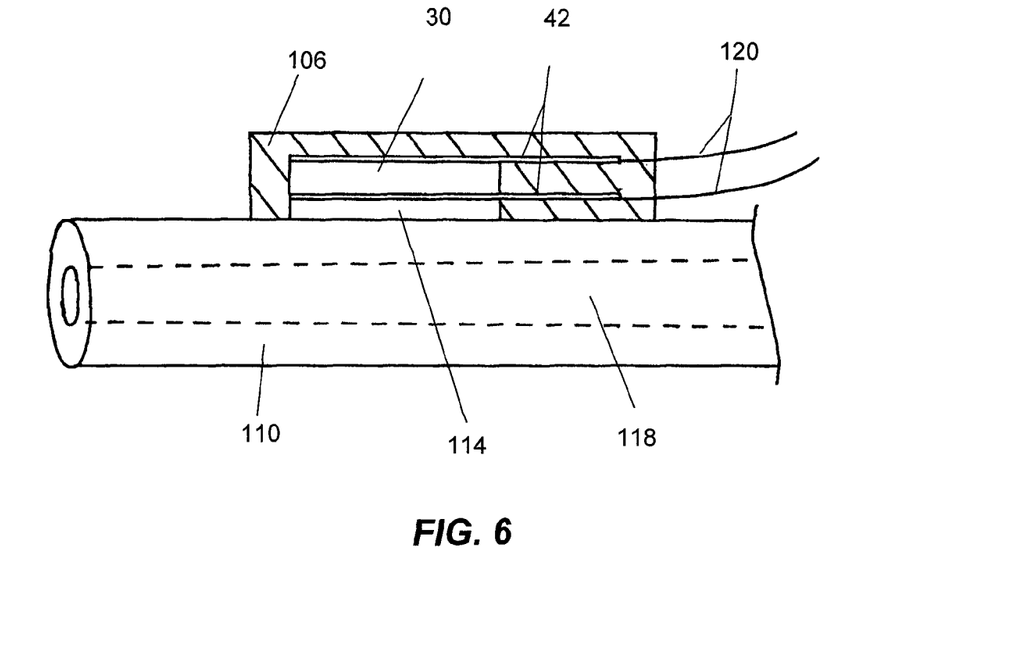
FIG. 6 shows the sensor of FIG. 2 used to detect the contents of a tube.
Figure 7:
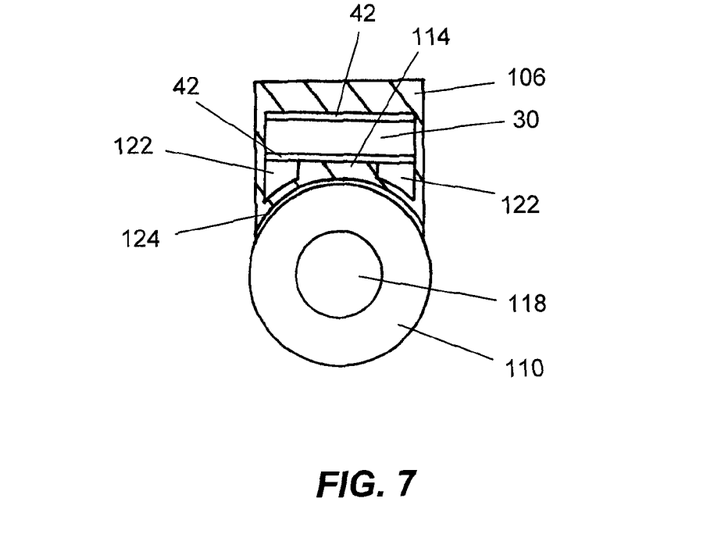
FIG. 7 shows an end view of the sensor of FIG. 6.

FIG. 6 shows a partially cut away side view of an ultrasonic sensor 30 used to detect fluid inside of a tube. The sensor 30 is typically encased in a housing 106 and attached to the tube 110. A pedestal 114 or mask may be used to control the width of the beam and direct the beam through the conduit 118 of the tube 110. FIG. 7 shows a partially cut away end view of the tube 110 and sensor 30. The pedestal 114 provides a transmission path for the ultrasonic signals and transmits the signals through the conduit 118 and not through the sidewalls of the tube, increasing the accuracy of the sensor. The areas 122 around the pedestal 114 may be voids so as to block the signals, or may be filled with a mask which prevents the transmission of ultrasonic signals, such as a foamed latex or other air bearing material. A compliant material 124 may be used between the housing 106 and the conduit 110, such as where the conduit is rigid.

For all of the inventive sensors shown herein, the exposed contacts 58 of the electrical leads formed as parts of the flex circuits 42 are attached to wires 120 (FIG. 6) and thereby attached to a driver circuit (or may be directly attached to a driver circuit). It is known in the art to create such a driver circuit for a piezoelectric sensor. The driver circuit will apply a voltage to the ceramic element 34 to cause the element to emit ultrasonic vibrations and will detect ultrasonic vibrations received by the sensor by detecting the voltage produced across the ceramic element. For simplicity, the electrical driver circuits are not shown herein.

The design of the sensor 30, including the flex circuits 42, allows for efficient transmission of ultrasonic signals and a quick ring down of the sensor, allowing the use of the sensor for detecting air or liquid in the tube 110. The sensor 30 is able to receive and detect the reflected signals which occur very quickly after the initial transmitted signal. As has been mentioned previously, constructing the sensor 30 with a thinner ceramic element 34 (such as an element with a 0.017 inch thickness) and using a thinner total thickness 70 of polyimide (such as 0.004 inch thick) will make the sensor 30 ring down even quicker, making the sensor better suited for single sensor detection of gas and liquid in very small conduits where a reflected signal will strike the sensor very quickly after transmitting the original signal.

Figure 8:
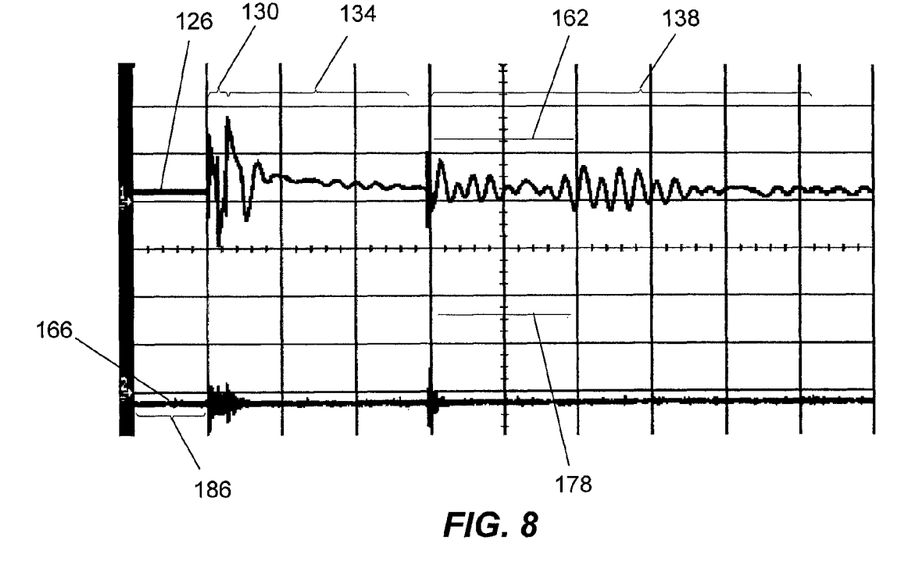
FIG. 8 shows the response of a sensor such as that of FIG. 6 with gas in the tube.

FIG. 8 shows the signal response 126 of the sensor 30 when gas is present in the conduit 118 of the tube 110. The initial transmitted signal 130 and the ring down period 134 of the sensor 30 are shown, as well as the signal 138 which is reflected back towards the sensor 30. It can be appreciated from the reflected signal 138 that the small size and non-planar shape of the tube 110 provides a somewhat irregular reflected signal 138.

Figure 9:
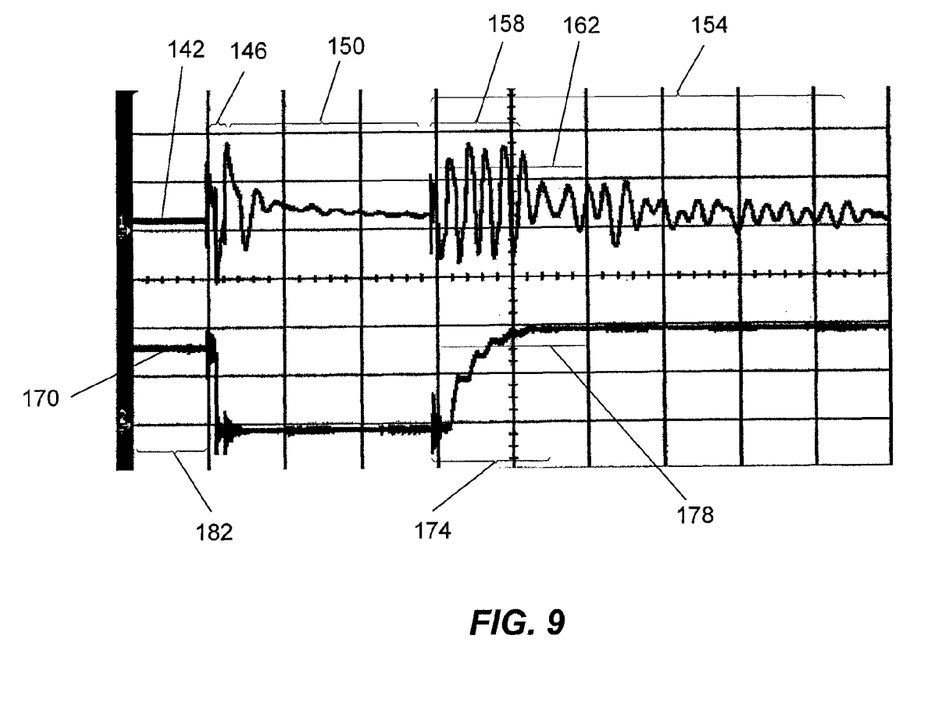
FIG. 9 shows the response of a sensor such as that of FIG. 6 with liquid in the tube.

FIG. 9 shows the signal response 142 of the sensor 30 when liquid is present in the conduit 118 of the tube 110. The initial transmitted signal 146 and the ring down period 150 are substantially the same as that of FIG. 8. The signal 154 reflected back towards the sensor 30, however, is different than that of FIG. 8. The reflected signal 154 shows a stronger initial signal 158 where the reflected signal 138 (gas present in the conduit 118) does not show a strong initial signal. This difference may be used to distinguish between liquid and gas in the conduit 118 adjacent the sensor.

The reflected signal 138, 154 (FIGS. 8 and 9 respectively) may be processed to determine the contents of the conduit and provide the appropriate output from the sensor electronics. According to a presently preferred method of processing the reflected signals, a threshold signal value 162 is established which is used to determine whether the signal 138, 154 represents gas or liquid in the conduit. Signals 158 which are greater than the threshold value 162 indicate liquid presents in the conduit, while signals 138 less than the threshold value 162 indicate gas in the conduit.

The measured signals 138, 154 are transmitted to an integrator circuit and used to generate an integrated output signal 166, 170. Signals 158 greater than the threshold value 162 are integrated and increase the value of the integrated output signal 170, as shown at 174. Signal 170 rises in amplitude during period 174 as the reflected signals 158 are greater than the threshold value 162. A second integrator threshold value 178 may be used to change a digital output from the driver circuit to a HI or LOW state to reflect gas or liquid in the conduit. A LOW digital output signal could represent gas in the conduit 118 with a HI digital output signal representing liquid in the conduit.

The integrated output signal 166, 170 is reset at the beginning of each scanning period (when the signal 130, 146 is transmitted from the sensor 30). Thus, integrated output signal 170 represents liquid present in the conduit 118 during successive scanning periods. Time period 182 represents a high integrated output signal corresponding to liquid in the conduit. At the beginning of a new scanning period, i.e. the transmission of signal 146, the integrated output signal is reset to a zero value. When the reflected signal 154 indicates the presence of liquid, at 158, the integrated output signal increases, at 174, and passes threshold 178 to indicate a liquid signal. Thus, a digital output signal would be in a continuous HI state due to the repeated detection of liquid in the conduit 118.

Integrated output signal 166 represents gas in the conduit 118 during successive scanning periods. Thus, the integrated output signal 166 is at a zero value during prior scanning period 186. The integrated output signal 166 is reset to a zero value at the beginning of the new scanning period (corresponding to the transmitted signal 130). As the reflected signal 138 does not cross the threshold 162, the integrated output signal 166 does not increase. As the integrated output signal does not cross threshold 178, the digital output signal remains in a LOW state, indicating gas in the conduit 118.

The sensor and related circuitry may thus operate to determine whether air or liquid is present in the conduit 118. The use of an amplitude threshold 162 for the reflected signal value and an amplitude threshold 178 for the integrated output signal value requires that the reflected signal 138, 154 have both sufficient intensity and sufficient duration to qualify as a valid signal. Presently, the digital output signal remains in a HI or LOW state to indicate gas or liquid in the conduit 118 during an entire scanning period according to the results of the previous scanning period. Such a configuration results in a time delay for changing the state of the digital output signal equal to the length of the scanning period, but makes the time duration of the various states of the digital output signal equal to the time duration of the scanning periods where the gas or liquid is detected, making the digital output signal valid in determining the relative amounts of time that gas or liquid were in the conduit 118.

Figure 10:
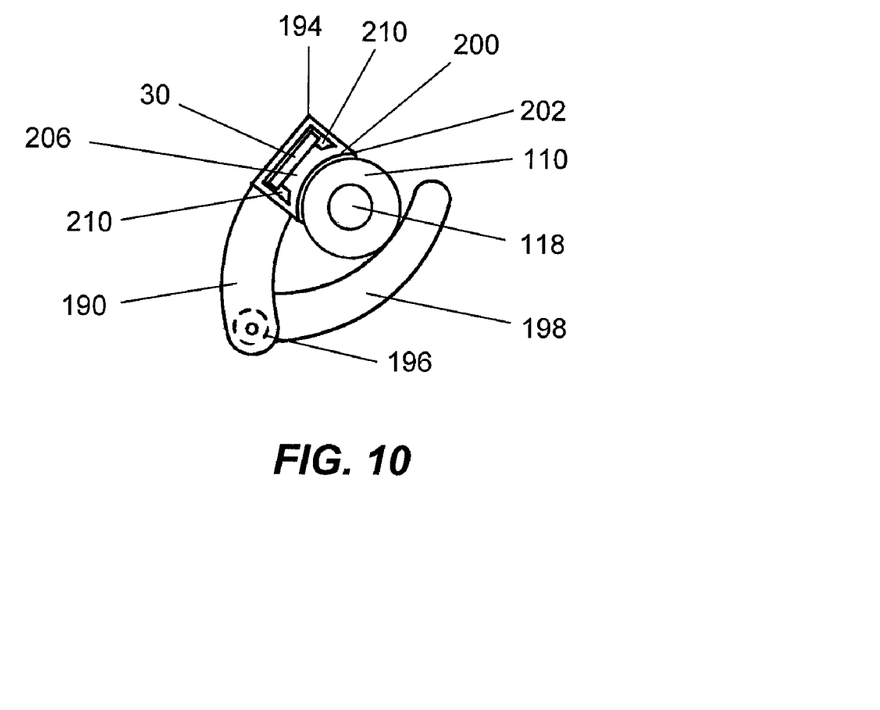
FIG. 10 shows an end view of a clip-on detector with the sensor of FIG. 2.

FIG. 10 shows another embodiment of the present sensor for detecting gas and liquid in a tube or small conduit. A clip type mount includes a first arm 190 which holds the sensor 30 in a housing 194 and a second arm 198 which holds the tube 110 (or other conduit) against the housing 194. The clip includes a spring or other biasing element 196 to bias the second arm 198 toward the first arm 190 to hold the tubing 110 against an engagement surface 200 of the housing 194. A compliant material 202, such as a soft rubber, may be used between the engagement surface 200 of the housing 194 and the tube 110 to increase the transmission of ultrasonic signals if desired. Such a compliant material 202 may be necessary where the tube 110 is rigid. The housing 194 may include a pedestal mount 206 and masked areas 210 (which may be filled with a material which blocks ultrasound) to limit the transmitted signals to a beam which passes through the conduit 118 of the tube 110.

The present sensor 30, by allowing for sensing gas or liquids in a conduit with a single sensor, allows for greatly simplified construction of such a clip on detector. Since detection only requires a single sensor 30, there is no concern about misalignment of a emitter and a detector, and alignment of the sensor 30 with the conduit 118 is simplified as the tube 110 only need be centered with respect to the housing 194. The clip on sensor will function as described above with respect to the tube mounted sensor.

Figure 11:
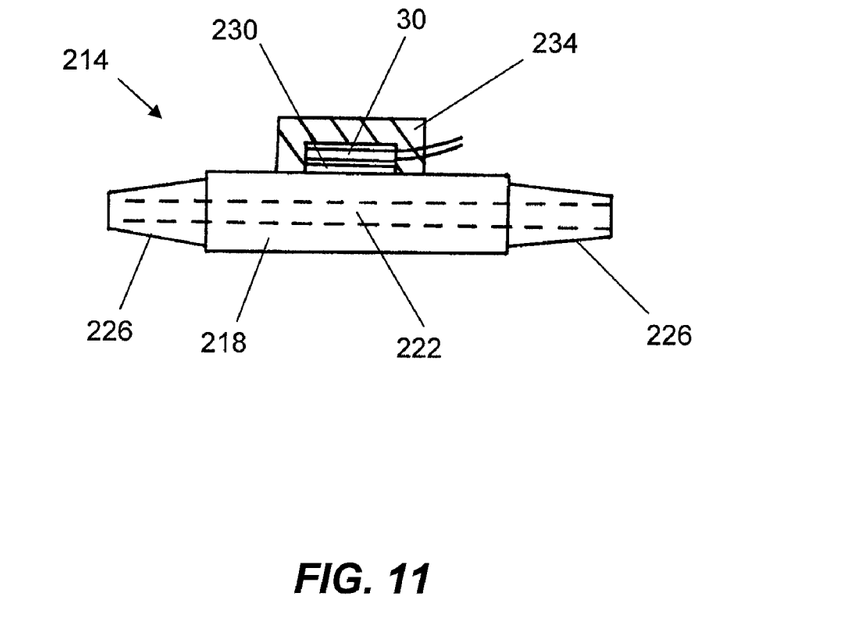
FIG. 11 shows a side view of a tubing coupler having the sensor of FIG. 2.
Figure 12:
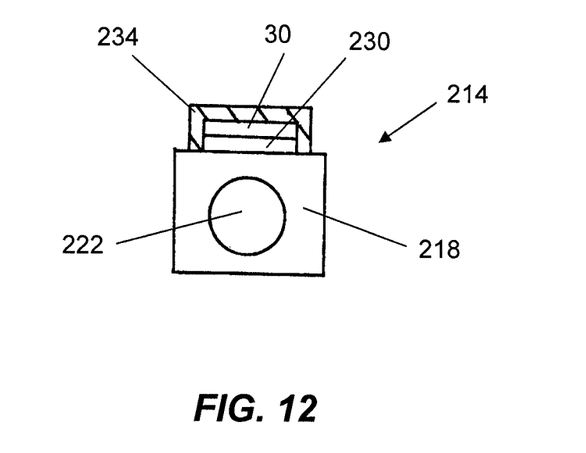
FIG. 12 shows an end view of the coupler of FIG. 11.

FIGS. 11 and 12 show partially cut away side and end views of a tube adaptor 214 with an ultrasonic sensor 30 according to the present invention. The adapter 214 includes a body 218 with a conduit 222 therethrough. The body 218 may have tube couplers 226 formed on the ends to allow tubing to be attached to the adapter. A sensor 30 is attached to the body 218, possibly via a pedestal 230 to control the width of the ultrasonic signal beam which is transmitted through the conduit 222. A housing 234 surrounds the sensor 30. The sensor will function substantially as described above with respect to the tube mounted detector.

Figure 13:
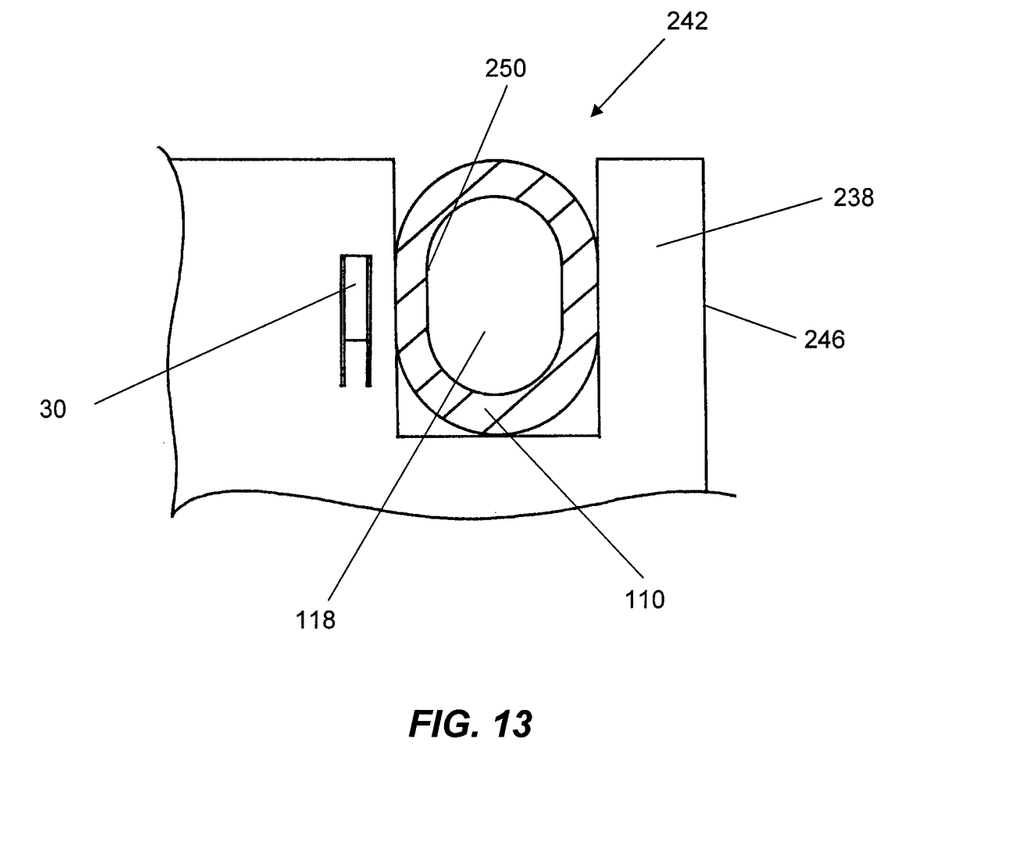
FIG. 13 shows the sensor of FIG. 2 used to monitor a tube in a channel.

FIG. 13 shows a partially cut away end view of a sensor 30 mounted inside of a housing 238. The housing has a channel 242 which receives a tube 110 having a conduit 118 through the tube. The housing 238 may be part of a fluid delivery pump, fluid monitoring system, or a universal gas/liquid detector for use with a tube. The sensor 30 is placed so as to direct ultrasonic signals through the conduit 118. A pedestal or mask areas may be used if necessary to limit the width of the ultrasonic beam to the width of the tube conduit 118. The far wall 246 of the housing is preferably smooth and parallel to the sensor 30, providing a good surface for reflecting ultrasonic signals back towards the sensor 30. Thus, if air is present in the conduit 118, the ultrasonic signal may be reflected off of the inside wall 250 of the tube 110. If liquid is present in the conduit 118, the ultrasonic signal will be transmitted through the liquid in the conduit 118, reflect off of the far wall 246, pass through the liquid again, and be received by the sensor 30. The passage of the ultrasonic signal through the liquid will diminish the signal somewhat, but the gain of the detection circuitry can be adjusted to compensate. The sensor should function as described above with respect to the tube mounted detector.

Figure 14:
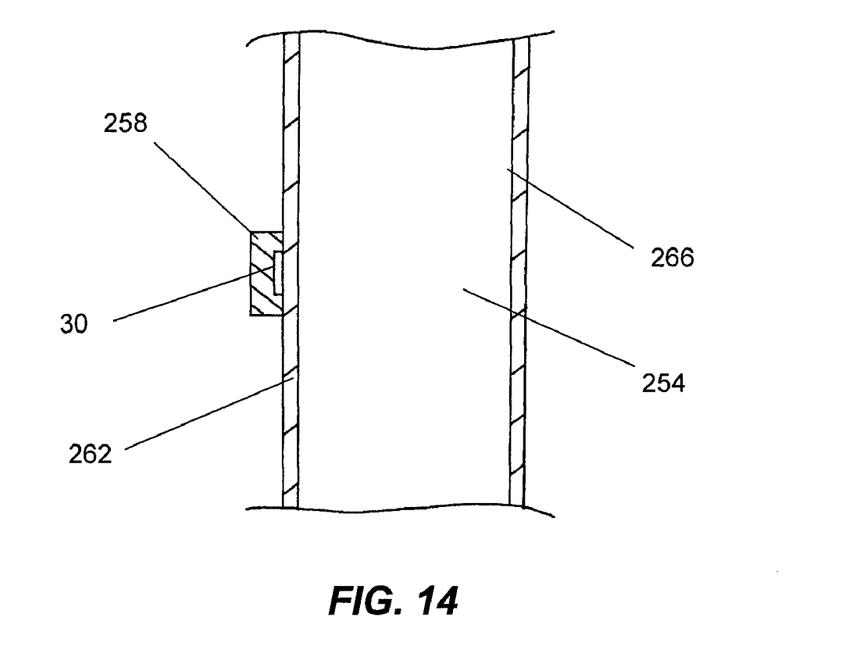
FIG. 14 shows a side view of a level detector having the sensor of FIG. 2.
Figure 15:
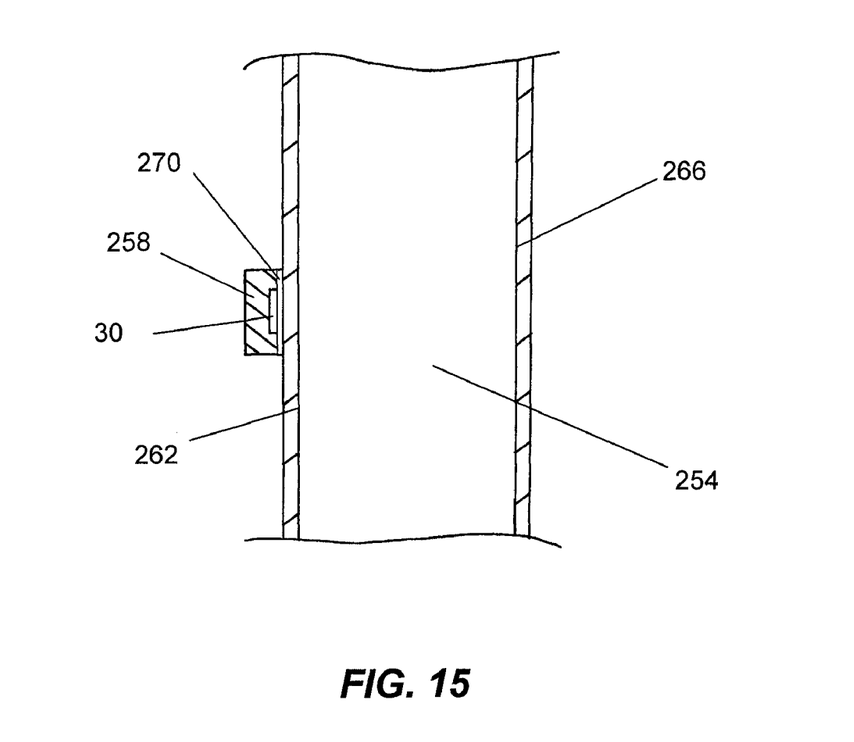
FIG. 15 shows a side view of a level detector having the sensor of FIG. 2.

FIGS. 14 and 15 show a sensor 30 of the present invention attached to a reservoir 254. The sensor 30 is typically contained within a housing 258. If the reservoir 254 is empty, or if gas is present in the reservoir opposite the sensor, the sensor may detect the transmitted ultrasonic signal reflected off of the near wall 262 of the reservoir. If the reservoir 254 is filled with liquid to the level of the sensor 30, the sensor may detect the ultrasonic signal reflected off of the far wall 266 of the reservoir. The reflected signal may be reduced in amplitude after passing through the liquid, but the detector circuit gain may be adjusted to compensate. Alternately, the sensor 30 may operate based off of the near wall reflection only.

The detector circuitry may be configured to detect a signal reflected off of the near wall 262 when air is present in the reservoir 254, and to identify the presence of liquid in the reservoir 254 based on the lack of a signal reflected off of the near wall. Such a configuration would be useful in a large reservoir where the signals reflected off of the far wall 266 may be too weak or dispersed for detection. The present invention facilitates near wall sensing because the flex circuits 42 provide good signal transmission from the ceramic element 34 and allow the sensor 30 to ring down quickly. As such, the sensor 30 is ready to detect reflected ultrasonic signals which arrive quickly after the transmitted signals as would occur with near wall reflections.

A further advantage of the sensor 30 having flex circuits 42 according to the present invention is the ability to increase the repetition rate of the sensor. The sensor 30 is capable of receiving reflected signals more quickly after the transmitted signal (due to the shorter ring down period of the sensor) such that shorter sensing geometries (distances across which the signal is transmitted, reflected, and received) may be enabled to speed up the overall send and receive process. The faster send and receive process (shorter send and receive period) of the sensor 30 allows more send and receive cycles during a given period of time, and thus allows the sensor to detect smaller variations in the fluid contained in the reservoir or conduit. As such, the sensor 30 is able to detect smaller gas bubbles in a liquid stream, smaller liquid amounts in a gas stream, detect gas or liquid in a faster moving fluid stream, or more quickly detect changes in a liquid level. Many situations demand fast detection, or detection of minute amounts of contamination in a stream, and the present sensor is better suited to detect such small changes.

As illustrated in FIG. 15, a sensor 30 may include a coupling material 270 such as a soft rubber to aid in coupling the housing 258 to the reservoir 254. This may be especially appropriate where the reservoir is slightly curved, or where the sensor 30 is removable from the reservoir 254.

Figure 16:
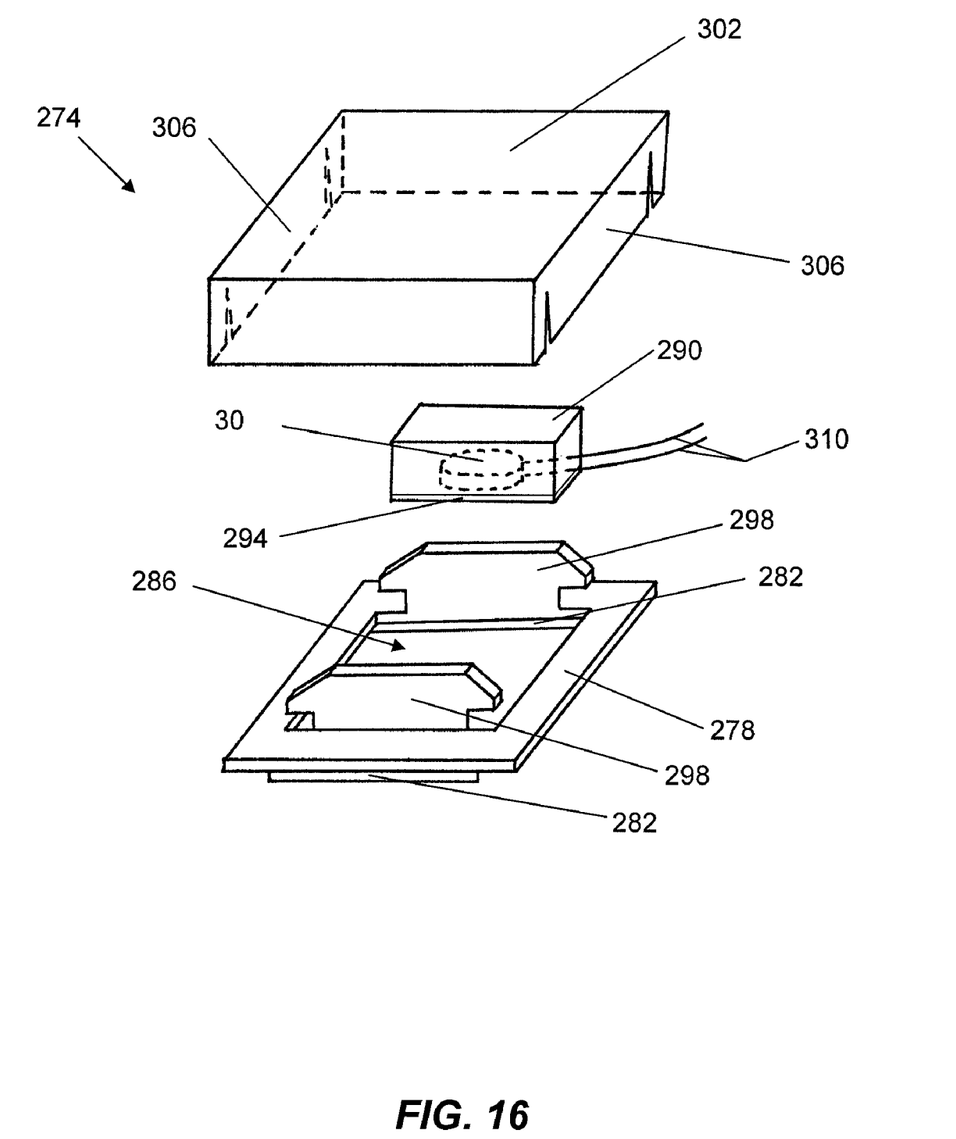
FIG. 16 shows a mounting clamp for attaching a sensor according to FIG. 2 to a reservoir.

FIG. 16 shows a disposable clip mount 274 which may be used to mount the sensor 30 of the present invention to a reservoir or conduit. The clip mount 274 includes a base 278 which is attached to a reservoir by adhesive, such as by double sided foam tape 282. The base 278 has an opening 286 formed therein to allow the detector housing 290 to directly contact the reservoir, typically via an acoustic coupling pad 294, such as a soft rubber pad. By allowing direct contact between the sensor housing 290 and the reservoir, the opening 286 provides for reliable ultrasonic signal transmission. The base 278 includes locking tabs 298 which engage a cap 302.

The cap 302 includes deflectable portions 306 which engage the tabs 298 so as to lock the cap in place over the base 278. The cap 302 and base 278 are sized to securely hold the sensor housing 290 against the reservoir and to cover and protect the sensor housing 290. The cap 302 may be removable from the base 278, and thus allow the sensor 30 to be reused. The cap 302 and base 278 may be quite inexpensive and thus disposable. Electrical leads 310 connect the sensor 30 to the driver circuits. The sensor 30 would function as discussed above and in particular with respect to FIGS. 14 and 15.

Figure 17:
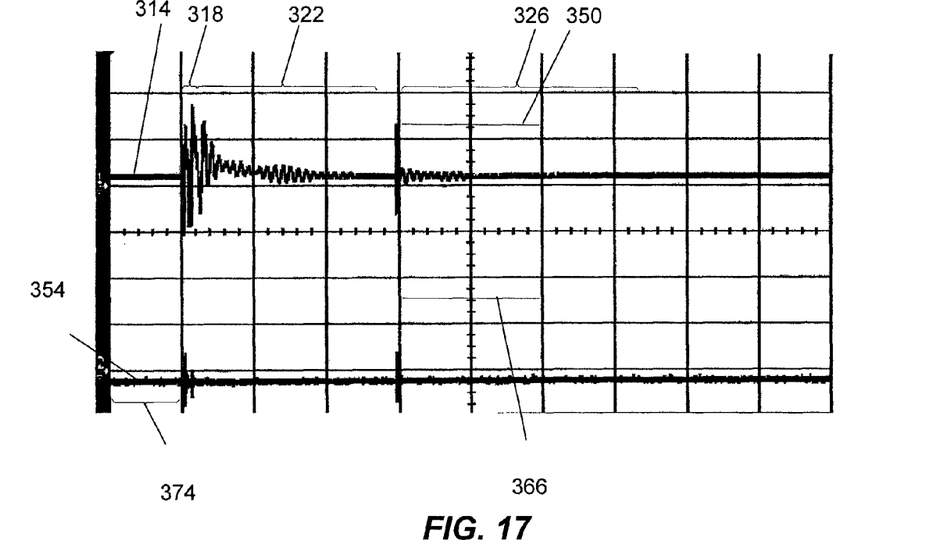
FIG. 17 shows the response of a sensor such as that of FIG. 14 with gas in the reservoir.

FIG. 17 shows the signal response 314 of the sensor 30 when gas is present in the reservoir 254. The initial transmitted signal 318 and the ring down period 322 of the sensor 30 are shown, as well as the small signal 326 which is reflected back towards the sensor 30.

Figure 18:
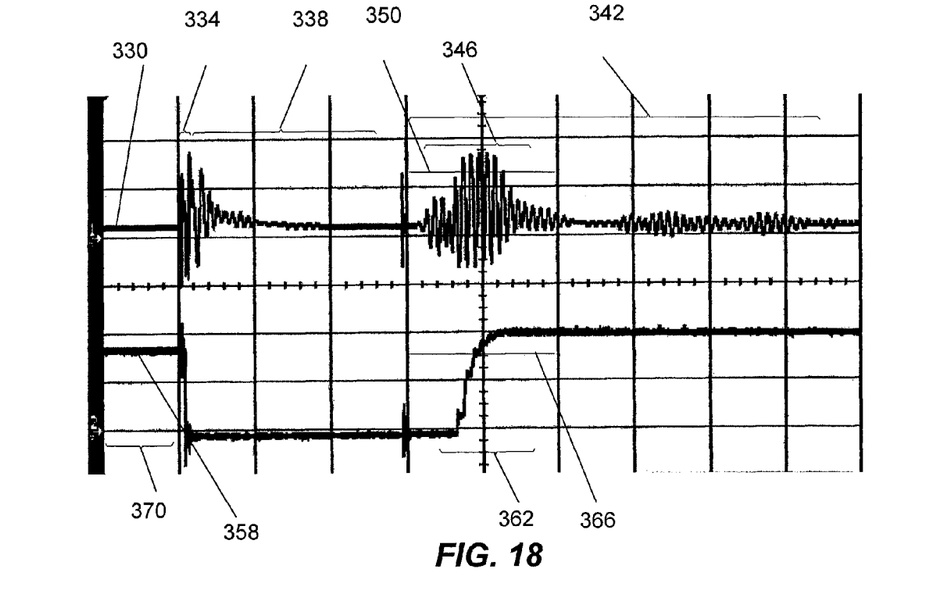
FIG. 18 shows the response of a sensor such as that of FIG. 14 with liquid in the reservoir.

FIG. 18 shows the signal response 330 of the sensor 30 when liquid is present in the reservoir 254. The initial transmitted signal 334 and the ring down period 338 are substantially the same as that of FIG. 17. The signal 342 reflected back towards the sensor 30, however, is different than that of FIG. 17. The reflected signal 342 shows a stronger initial signal 346 where the reflected signal 326 (gas present in the reservoir 254) does not show a strong initial signal. This difference may be used to distinguish between liquid and gas in the reservoir 254 adjacent the sensor.

The reflected signal 326, 342 may be processed to determine the contents of the conduit and provide the appropriate output from the sensor electronics. According to a presently preferred method of processing the reflected signals, a threshold signal value 350 (or pair of threshold values) is established which is used to determine whether the signal 326, 342 represents gas or liquid in the conduit. Signals 346 which are greater than the threshold value 350 indicate liquid present in the conduit, while signals less than the threshold value 350 indicate gas in the conduit.

The measured signals 326, 342 are transmitted to an integrator circuit and used to generate an integrated output signal 354, 358. Signals 346 greater than the threshold value 350 are integrated and increase the value of the integrated output signal 358, as shown at 362. Signal 358 rises in amplitude during period 362 as the reflected signals 346 are greater than the threshold value 350. A second integrator threshold value 366 may be used to change a digital output from the driver circuit to a HI or LOW state to reflect gas or liquid in the conduit. A LOW digital output signal could represent gas in the reservoir 254 with a HI digital output signal representing liquid in the reservoir.

The integrated output signal 354, 358 is reset at the beginning of each scanning period (when the signal 318, 334 is transmitted from the sensor 30). Thus, integrated output signal 358 represents liquid present in the reservoir 254 during successive scanning periods. Time period 370 represents a high integrated output signal corresponding to liquid in the conduit. At the beginning of a new scanning period, i.e. the transmission of signal 334, the integrated output signal is reset to a zero value. When the reflected signal 342 indicates the presence of liquid, at 346, the integrated out signal increases, at 362, and passes threshold 366 to indicate a liquid signal. Thus, a digital output signal would be in a continuous HI state due to the repeated detection of liquid in the reservoir 254.

Integrated output signal 354 represents gas in the reservoir 254 during successive scanning periods. Thus, the integrated output signal 354 is at a zero value during prior scanning period 374. The integrated output signal 354 is reset to a zero value at the beginning of the new scanning period (corresponding to the transmitted signal 318). As the reflected signal 326 does not cross the threshold 350, the integrated output signal 354 does not increase. As the integrated output signal 354 does not cross threshold 366, the digital output signal remains in a LOW state, indicating gas in the reservoir 254.

The sensor and related circuitry may thus operate to determine whether air or liquid is present in the reservoir 254. The use of an amplitude threshold 350 for the reflected signal value and an amplitude threshold 366 for the integrated output signal value requires that the reflected signal 326, 342 have both sufficient intensity and sufficient duration to qualify as a valid signal. Presently, the digital output signal remains in a HI or LOW state to indicate gas or liquid in the reservoir 254 during an entire scanning period according to the results of the previous scanning period. Such a configuration results in a time delay for changing the state of the digital output signal equal to the length of the scanning period, but makes the time duration of the various states of the digital output signal equal to the time duration of the scanning periods where the gas or liquid is detected, making the digital output signal valid in determining the relative amounts of time that gas or liquid were in the reservoir 254.

There is thus disclosed an improved ultrasonic gas and liquid detector. It will be appreciated that numerous changes may be made to the present invention without departing from the scope of the claims.

What is claimed is:

1. An ultrasonic sensor comprising:
   a ceramic element, the ceramic element being planar and having a first side and a second side opposite the first side, the ceramic element having a first metal layer disposed on the first side thereof and a second metal layer disposed on the second side thereof;
   a first flex circuit comprising a polyimide layer and an electrically conductive metal contact layer disposed on the polyimide layer, the first flex circuit having a mounting pad having holes formed through the metal contact layer and being attached to the ceramic element such that the contact layer and the holes are placed in contact with the first metal layer on the ceramic element; and
   a second flex circuit comprising a polyimide layer and an electrically conductive contact layer disposed on the polyimide layer, the second flex circuit having a mounting pad having holes formed through the metal contact layer and being attached to the ceramic element such that the contact layer and the holes are placed in contact with the second metal layer on the ceramic element.

2. The sensor of claim 1, wherein the first flex circuit comprises a first portion having a shape corresponding to the shape of the ceramic element and a second portion extending therefrom so as to form an electrical lead configured for connection to a driver circuit, and wherein the second flex circuit comprises a first portion having a shape corresponding to the shape of the ceramic element and a second portion extending therefrom so as to form an electrical lead configured for connection to a driver circuit.

3. The sensor of claim 1, wherein the ceramic element is circular, and wherein the first flex circuit comprises a first portion which is circular and configured for engaging the ceramic element and a second portion which is elongate and configured for attachment to a driver circuit and wherein the second flex circuit comprises a first portion which is circular and configured for engaging the ceramic element and a second portion which is elongate and configured for attachment to a driver circuit.

4. The sensor of claim 2, wherein the thickness of the polyimide layer in the first portion of the first flex circuit is approximately one fourth the thickness of the ceramic element and wherein the thickness of the polyimide layer in the first portion of the second flex circuit is approximately one fourth the thickness of the ceramic element.

5. The sensor of claim 1, wherein the first flex circuit is attached to the first side of the ceramic element with adhesive and wherein the second flex circuit is attached to the second side of the ceramic element with adhesive.

6. The sensor of claim 5, wherein the adhesive is an anisotropic epoxy.

7. The sensor of claim 1, wherein, for the first and second flex circuits, the electrically conductive contact layer comprises a copper layer.

8. A fluid detection system comprising the sensor of claim 1, and further comprising a clip for holding the sensor adjacent a tube, the clip comprising:
 a first arm having a first end and a second end, the first end having the sensor mounted thereto and having an engagement surface configured for engaging the tube and positioning the tube in alignment with the sensor;
 a second arm pivotably attached to the second end of the first arm and biased towards the first arm so as to hold the tube adjacent the engagement surface.

9. A fluid detection system comprising the sensor of claim 1, and further comprising a tube adapter, the adapter comprising:
 an elongate body having a bore therethrough;
 a first tube coupler disposed on a first end of the body and configured for attaching a tube to the coupler such that the tube is in fluid communication with the bore;
 a second tube coupler disposed on a second end of the body and configured for attaching a tube to the coupler such that the tube is in fluid communication with the bore; and
 wherein the sensor is attached to the body such that ultrasonic signals emitted from the sensor are passed through the bore.

10. A fluid detection system comprising the sensor of claim 1, and further comprising a clip mount for attaching the sensor to a reservoir, the clip mount comprising:
 a base, the base being attachable to a reservoir; and
 a cap, the cap being configured for engaging the base so as to be attachable to the base and so as to hold the sensor in contact with the reservoir.

11. The system of claim 10, wherein the base has an opening therein so as to allow the sensor to contact the reservoir.

12. The system of claim 11, wherein the sensor is disposed in a housing.

13. The system of claim 12, wherein an acoustic coupling pad is placed between the sensor housing and the reservoir.

14. An ultrasonic sensor comprising:
 a ceramic element, the ceramic element being planar so as to form a first side and a second side, the second side being opposite the first side;
 a first metal layer disposed on the first side of the ceramic element;
 a second metal layer disposed on the second side of the ceramic element;
 a first flex circuit comprising an insulating layer and a metal contact layer disposed on the insulating layer, the metal layer comprising a metal mounting pad, holes formed in the mounting pad, and an arm extending from the mounting pad, the arm forming an electrical lead, the first flex circuit being attached to the ceramic element such that the mounting pad and the holes are placed in contact with the first metal layer on the ceramic element; and
 a second flex circuit comprising an insulating layer and a metal contact layer disposed on the insulating layer, the metal layer comprising a metal mounting pad, holes formed in the mounting pad, and an arm extending from the mounting pad, the arm forming an electrical lead, the second flex circuit being attached to the ceramic element such that the mounting pad and the holes are placed in contact with the second metal layer on the ceramic element.

15. The ultrasonic sensor of claim 14, wherein, for the first and second flex circuits, the insulating layer is formed from at least one polyimide layer.

16. The ultrasonic sensor of claim 14, wherein, for the first and second flex circuits, the insulating layer has a thickness which is approximately one fourth of the thickness of the ceramic element.

17. An ultrasonic sensor comprising:
 a ceramic element, the ceramic element being planar so as to form a first side and a second side, the second side being opposite the first side;
 a first metal layer disposed on the first side of the ceramic element;
 a second metal layer disposed on the second side of the ceramic element;
 a first flex circuit comprising an insulating layer and a metal contact layer disposed on the insulating layer, the first flex circuit being attached to the ceramic element such that the metal contact layer is placed in contact with the first metal layer on the ceramic element; and
 a second flex circuit comprising an insulating layer and a metal contact layer disposed on the insulating layer, the second flex circuit being attached to the ceramic element such that the metal contact layer is placed in contact with the second metal layer on the ceramic element; and
 wherein the first and second flex circuit more specifically comprise:
 a metal layer, the metal layer including a mounting pad having a size and shape corresponding to the size and shape of the ceramic element and an arm extending therefrom to form an electrical lead;
 a plurality of holes formed in the mounting pad;
 a polyimide layer attached to the metal layer, the polyimide layer covering at least the mounting pad;
 wherein the metal layer mounting pad is attached to the ceramic element such that the mounting pad holes are disposed in contact with one of the first and second metal layers; and
 an insulating layer disposed to cover a portion of the arm.

18. The ultrasonic sensor of claim 17, wherein the polyimide layer attached to the pad is approximately one fourth the thickness of the ceramic element.

* * * * *